US009868922B2

(12) United States Patent
Aaltonen et al.

(10) Patent No.: US 9,868,922 B2
(45) Date of Patent: Jan. 16, 2018

(54) METHOD FOR RECOVERY OF OIL FROM BIOMASS

(75) Inventors: Olli Aaltonen, Helsinki (FI); Olli Jauhiainen, Espoo (FI); Mervi Hujanen, Helsinki (FI)

(73) Assignee: NESTE OYJ, Espoo (FI)

( * ) Notice: Subject to any disclaimer, the term of this patent is extended or adjusted under 35 U.S.C. 154(b) by 1568 days.

(21) Appl. No.: 13/291,577

(22) Filed: Nov. 8, 2011

(65) Prior Publication Data

US 2012/0116105 A1 May 10, 2012

Related U.S. Application Data

(60) Provisional application No. 61/411,134, filed on Nov. 8, 2010.

(30) Foreign Application Priority Data

Nov. 8, 2010 (EP) .................................... 10190307

(51) Int. Cl.

| | |
|---|---|
| ***C09K 3/00*** | (2006.01) |
| ***C07C 69/00*** | (2006.01) |
| ***B01D 11/02*** | (2006.01) |
| ***C11B 1/10*** | (2006.01) |
| ***C11B 1/02*** | (2006.01) |

(52) U.S. Cl.
CPC . *C11B 1/10* (2013.01); *C11B 1/02* (2013.01)

(58) Field of Classification Search
None
See application file for complete search history.

(56) References Cited

U.S. PATENT DOCUMENTS

| | | | |
|---|---|---|---|
| 4,331,695 | A | 5/1982 | Zosel |
| 4,857,329 | A | 8/1989 | Sako et al. |
| 2003/0143659 | A1 | 7/2003 | Bijl et al. |
| 2008/0188676 | A1 | 8/2008 | Anderson et al. |
| 2010/0050502 | A1 | 3/2010 | Wu et al. |
| 2010/0233761 | A1 | 9/2010 | Czartoski et al. |

FOREIGN PATENT DOCUMENTS

| | | | |
|---|---|---|---|
| CA | 2165387 | A1 | 6/1996 |
| CN | 10271100 | A | 5/2011 |
| WO | WO 2006/085672 | A2 | 8/2006 |
| WO | WO 2006/136539 | A1 | 12/2006 |
| WO | WO 2008/034109 | A1 | 3/2008 |
| WO | WO 2010/021753 | A1 | 2/2010 |
| WO | WO 2011/109852 | A1 | 9/2011 |

OTHER PUBLICATIONS

Notification of Transmittal of the International Search Report (Form PCT/ISA/220 and PCT/ISA 210) and the Written Opinion of the International Searching Authority (Form PCT/ISA/237) dated Feb. 16, 2012, issued in the corresponding International Application No. PCT/FI2011/050982. (13 pages).
Extended European Search Report issued in European Application No. 10190307.8-1221, on Apr. 14, 2011.
Ronald Halim et al., "Oil Extraction From Microalgae for Biodiesel Production", Bioresource Technology, vol. 102, No. 1, Jul. 23, 2010, pp. 178-185, XP-027368474.

*Primary Examiner* — David W Berke-Schlessel
(74) *Attorney, Agent, or Firm* — Buchanan Ingersoll & Rooney PC

(57) ABSTRACT

A method and apparatus for recovery of lipids from microbial biomass, including providing wet microbial biomass to thermal pretreatment of at least 100° C. in a pressure vessel, subjecting the thermally pretreated microbial biomass to extraction using a liquid hydrocarbon as an extractant, and subsequently, recovering a product containing lipids.

22 Claims, 3 Drawing Sheets

METHOD FOR RECOVERY OF OIL FROM BIOMASS

CROSS-REFERENCE TO RELATED APPLICATIONS

This application claims priority to European Patent Application No. 10190307.8, filed Nov. 8, 2010, and U.S. Provisional Patent Application No. 61/411,134, filed Nov. 8, 2010, wherein the contents of each of the above applications are incorporated herein by reference.

FIELD

Disclosed is a method for recovering lipids from microbial biomass using extraction.

BACKGROUND

Microorganisms such as algae, bacteria or fungi may contain triglycerides up to 80% of their total dry matter content. However, oil from microbial biomass which is suitable as precursor for fuel production is scarce on the market. This is mainly due to lack of efficient and economical methods for providing good quality oil from microbial biomass.

The available methods for extracting oil or lipids from microbial biomass typically require the biomass to be dried and/or the microbial cells to be disrupted. Drying of the biomass consumes much energy and is, for example, performed by heating or freeze-drying, or even spray drying is used. The typical water content or the dry matter content of the biomass is dependent on the microbial material used. Typically dry matter contents from 15% up to 40% can be achieved by traditional cell harvesting techniques such as centrifugation or filtration. Essentially, it is typically aimed at as low free water content as possible in order to maximize the extraction yields.

One alternative method to acquire oil from biomass is to apply non-selective extractants which typically produces oil containing high amounts of impurities. Impurities such as metals, phosphorus and amino acids cause problems e.g. in catalytic fuel production in form of catalyst poisons and/or corrosive materials. Therefore, it is often required to use post processing for removal of these undesired components from the extracted oil product.

In general, methods available suffer either from lack of selectivity to produce good quality oil or poor yield which are compensated by additional processing steps or selection of uneconomical processing conditions.

One of the commonly used extractants for retrieval of oils from oil containing materials is carbon dioxide in subcritical or preferably supercritical state. Unfortunately carbon dioxide has a weak dissolving capacity towards vegetable neutral lipids. This property has been modified by incorporation of entraining agents exhibiting better dissolution such as propane or butane. Supercritical fluids have better dissolution capacities but require high operating pressures. Moreover, the extraction times also tend to remain uneconomically long.

CA-2165387 discloses a selective extraction of fats and/or oils from solid natural materials, such as microbial solids, like dried and pelletized fermentation residues having water content less than 5%, with compressed gases. The extraction is carried out using a mixture of propane and maximum of 50% by weight of carbon dioxide at temperatures below 96° C. and pressures below 73 bar. These two pure gases each are in the subcritical state. In this method an energy consuming drying step prior to the extraction is carried out.

U.S. Pat. No. 4,331,695 discloses a method for extracting fats or oils from animal or vegetable products, such as soya flakes or maize, by contacting the product with a hydrocarbon solvent, such as propane, in the liquid phase and at a temperature below the critical temperature, separating the solvent containing extracted fat or oil from the residue of the product, and precipitating the extracted fat or oil from the solvent by heating the solvent to above the critical temperature of the solvent without taking up heat of vaporization. The resulting fat or oil is suitable for use in foodstuffs without further processing to remove solvent. The temperatures of propane may be 0-100° C. during extraction and 50-200° C. during precipitation of oil and fat, and the pressure may be the same during extraction and precipitation. The disclosed method does not disclose any pretreatment of the material to be extracted and the method does not include extraction of microbial biomass.

Occasionally, when extracting oil from microbial biomass mechanical disruption, dissemination or crushing of biomass cells has been used or even microwave assisted disruption of biomass cells to aid in increasing the extracted oil yield.

US-2003/0143659 discloses a process for isolation of compounds such as polyunsaturated fatty acids from microorganisms, in which process the biomass is first granulated and subsequently dried before extraction of the biomass. The biomass can be pasteurised in the growth medium, i.e. heated to 60-100° C., typically preferably to 96° C., up to 90 minutes in order to kill the micro-organism and also to deactivate enzymes which might otherwise destroy the fatty acids. The pasteurisation has no reported effect on the subsequent extraction.

WO2006136539 discloses an extraction process where lipids are obtained from wet biomass. In this process a desiccant is added to the wet biomass prior to extration to remove excess water. The biomass is pasteurised at 65° C. for 1 h prior to the extraction process.

SUMMARY

Provided is an industrially feasible method for fast and efficient lipid acquisition using a reasonable amount of extractant. The yield may be enhanced by adjustment of extraction time and used extractant amount. However, the process economics will eventually determine the suitable or desired yield efficiency.

Provided is a method for acquiring lipids from wet microbial biomass.

Provided is a selective method for acquiring lipids from microbial biomass for producing oil suitable for fuel production refining as such, especially for catalytic refining.

Provided is an efficient method acquiring lipids from microbial biomass with high yield.

The inventors have found that it is not necessary to dry the wet microbial biomass before extraction. Applying a thermal pretreatment to the biomass before extraction with a liquid hydrocarbon such as propane provides neutral lipids with high selectivity and good yield. The method according to the present invention thus provides a very high dissolving capability and excellent selectivity resulting in a lipid product with good yield and no or only little need for post extraction purification. Good quality lipids and/or oil is produced which may be used for feed of catalytic refining processes such as for renewable diesel, biodiesel or lubricant production. The recovered lipid and/or oil product has a low metal and phosphorus content.

The present invention provides a method for recovering lipids from microbial biomass as depicted by claim 1. Furthermore, an apparatus for use in said method is depicted by claim 11 and a method for recovery of lipids from microbial biomass using such an apparatus is depicted in claim 13.

Phospholipids typically tend to accumulate into the oil phase together with the neutral lipids when extracting microbial biomass. Surprisingly, applying a thermal pretreatment before extraction good quality oil is obtained containing a low amount of phosphorus. The obtained extracted product thus mainly contains fats in triglyceride form. The obtained product does not contain polar lipids, such as phospholipids, or other polar compounds. This significantly reduces the need for subsequent purification treatments of the obtained lipids.

The lipid product obtained by the process according to the present invention is also essentially free of metals. Even though many of the micro-organisms contain high amounts of various metals which typically are extracted in form of salts, the lipid product obtained by the process according to the invention does not essentially contain metals. Metals and phosphorus cause significant problem in further catalytic processes such as fuel production from the lipid product and would otherwise require extensive subsequent purification steps.

Furthermore, the possibility of extracting wet microbial biomass removes the need of additional water removal step prior to extraction thus saving processing time and costs. The processing duration for extraction remains short and the extraction is efficient. Water may be removed from microbial biomass by decantation or filtration without e.g. evaporation.

A further advantage is that no microbial cell disruption, such as mechanical grinding or the like, is required before processing the biomass. The lipids therein become available for extraction without any particular disruption step.

The method according to the current invention provides a process for extraction of lipids from microbial biomass with excellent effective yield. An economically sufficient lipid yield is obtained in a short extraction time using fairly low amount of extractant requiring small volume extraction apparatus. The initial part of the extraction curve shows a steep rise i.e. the value of the first derivative is larger than would have been expected.

DETAILED DESCRIPTION

Figure 1:
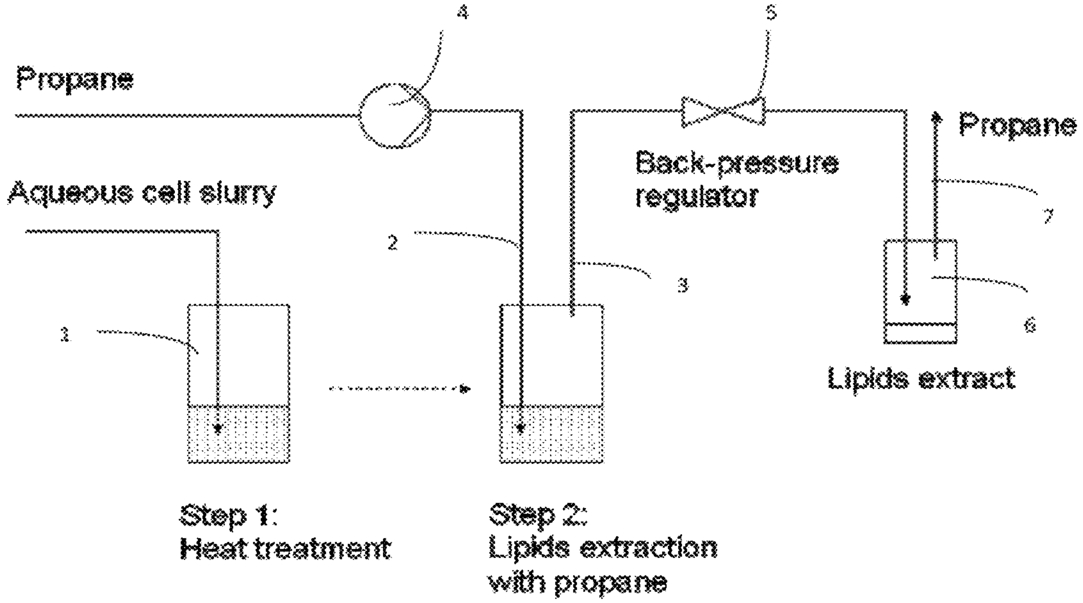
FIG. 1 shows a schematic view of the apparatus set-up used in examples 1, 2 and 3.

The term “lipid” refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids comprise, for example, fats, oils, waxes, wax esters, sterols, terpenoids, isoprenoids, carotenoids, polyhydroxyalkanoates, fatty acids, fatty alcohols, fatty acid esters, phospholipids, glycolipids, sphingolipids and acylglycerols, such as monoglyserides (monoacylglycerol), diglycerides (diacylglycerol) or triglycerides (triacylglycerol).

In the present invention desired lipids to be recovered in the product include fats, oils, waxes and fatty acids and their derivatives.

By the term “microbial biomass” is meant biomass derived from or containing microorganisms including bacteria, cyanobacteria, fungi such as yeasts, filamentous fungi and moulds, archaea, protists, microscopic plants such as algae or microalgae, plankton and the planarian. Most microorganisms are unicellular i.e. single-celled, however, some multicellular organisms are also microscopic. The microorganisms readily accumulate lipids or have been genetically modified to accumulate lipids or to improve accumulation of lipids.

In a preferred embodiment of the present invention lipid containing microbial biomass is selected from the group of bacteria, cyanobacteria, fungi such as yeasts, filamentous fungi and moulds, archaea, protists, microscopic plants such as algae, microalgae, plankton and planarian, more preferably microalgae, bacteria, fungi such as yeasts, filamentous fungi and moulds.

In a preferred embodiment the microbial biomass comprises microalgae genera comprising *Dunaliella, Chlorella, Botryococcus, Brachiomonas, Chlorococcum, Cryptheco-dinium, Euglena, Haematococcus, Chlamydomas, Isochrysis, Pleurochrysis, Pavlova, Prototheca, Phaeodactylum, Pseudochlorella, Parachlorella, Bracteococcus, Scenedesmus, Skeletonema, Chaetoceros, Nitzschia, Nannochloropsis, Navicula, Nannochloris, Scihizochytrium, Sceletonema, Thraustochytrium, Ulkenia, Tetraselmis* and *Synechocystis*. The method was found to be particularly effective with microalgae selected from the group consisting of *Nannochloropsis* sp., *Dunaliella* sp. such as *Dunaliella tertiolecta; Phaeodactylum* sp. such as *Phaeodactylum tricornutum*; and *Chlorella* sp. such as *Chlorella pyrenoidosa* capable of incorporating a high lipid content.

In another preferred embodiment the microbial biomass comprises filamentous fungal species belonging to the following genera *Aspergillus, Mortierella, Chaetomium, Claviceps, Cladosporidium, Cunninghamella, Emericella, Fusarium, Glomus, Mucor, Paecilomyces, Penicillium, Pythium, Rhizopus, Trichoderma, Zygorhynchus, Humicola, Cladosporium, Malbranchea, Ustilago* especially those species capable of accumulating high amounts of lipids and essential fatty acids. Preferably, microbial biomass comprises *Mortierella isabellina, Mucor, Aspergillus* or *Rhizopus*.

In yet another preferred embodiment the microbial biomass comprises oleaginous yeast belonging to the following genera *Clavispora, Deparyomyces, Pachysolen, Kluyveromyces, Galactomyces, Hansenula, Saccharomyces, Waltomyces, Endomycopsis, Cryptococcus*, such as *Cryptococcus curvatus, Rhodosporidium*, such as *Rhodosporidium toruloides, Rhodotorula*, such as *Rhodotorula glutinis, Yarrowia*, such as *Yarrowia lipolytica, Pichia*, such as *Pichia stipitis, Candida* such as *Candida curvata, Lipomyces* such as *Lipomyces starkeyi* and *Trichosporon* such as *Trichosporon cutaneum* or *Trichosporon pullulans* which readily accumulate lipids or have been genetically modified to improve lipid accumulation and/or production of lipids. Most preferably yeasts comprise *Lipomyces, Rhodosporidium*, or *Cryptococcus*.

In yet another preferred embodiment the microbial biomass comprises bacteria belonging to the following genera *Acinetobacter, Actinobacter, Alcanivorax, Aerogenes, Ana-*

*baena, Arthrobacter, Bacillus, Clostridium, Dietzia, Gordonia, Escherichia, Flexibacterium, Micrococcus, Mycobacterium, Nocardia, Nostoc, Oscillatoria, Pseudomonas, Rhodococcus, Rhodomicrobium, Rhodopseudomonas, Shewanella, Shigella, Streptomyces* and *Vibrio*. Most preferably bacteria comprise *Rhodococcus opacus, Acinetobacter, Nocardia* or *Streptomyces*.

In the first aspect of the present invention a method for the recovery of lipids from microbial biomass is provided. The method comprising at least the steps of (i) Providing wet microbial biomass to thermal pretreatment of at least 100° C.

(ii) Subjecting said thermally pretreated microbial biomass to extraction using a liquid hydrocarbon as an extractant. Preferred liquid hydrocarbons are nonpolar substances which are mainly or totally insoluble in water.

(iii) Subsequently, the product containing lipids is recovered.

The biomass to be processed may be obtained directly from cultivation or growth system such as bioreactor. Biomass to be processed, preferably microalgae biomass, is treated by generally known methods, such as filtration, decanting, flotation or sedimentation possible assisted by flocculation, to remove excess water or aqueous growth solution. Algae, mould or yeast biomass is preferably filtered or centrifuged before processing. On the other hand, biomass from immobilized cultivation or the like may be used by slurrying it into aqueous media.

By the term "wet" is meant microbial biomass which originates from aqueous cultivation solution and from which excess water is removed by common low energy consuming water removal processes such as filtering, centrifugation or sedimentation or the like and which is not specifically dried. Alternatively, solid dry microbial biomass may be slurried into an aqueous form.

After removal of excess water from the biomass to be treated by the method of the present invention the dry matter content of the biomass is typically below 70% by weight. Depending on the aqueous microbial biomass to be treated the dry matter content may be low, such as 4%. However, preferably the dry matter content is at least 5%, more preferably at least 15%, most preferably at least 19%, such as over 20%.

According the present invention the wet microbial biomass provided to a treatment apparatus is thermally pretreated before extraction of the lipids therein. Before starting the thermal pretreatment the volume of the treatment apparatus, preferably a pressure vessel, is purged with inert gas, preferably nitrogen, to avoid or minimize possible reactions with ambient gas. The pretreatment temperature is more than 100° C., preferably at least 120° C., more preferably from 120° C. to 300° C., most preferably from 150° C. to 250° C., such as from 160° C. to 220° C. The pressure inside the closed pretreatment vessel will settle according to the vapour pressure of the wet microbial biomass to be treated.

The microbial biomass mixture is preferably continuously agitated during the thermal pretreatment to enable uniform temperature across the mixture.

The temperature increase rate from the starting temperature to the pretreatment temperature may vary depending on the heat sources used and on the microbial biomass to be treated. Suitable, but not optimized, heating rate for at least algae, yeast and mould biomass is from 1° C./min to 2° C./min.

According to one embodiment the thermal pretreatment time is less than 180 min, preferably less than 120 min, such as about 100 minutes.

In a preferred embodiment after the pretreatment step the biomass is allowed to cool down, preferably to a temperature below 97° C., more preferably below 80° C., most preferably below 65° C. such as to the temperature set by the subsequent extraction step, before extraction is started. The method according to the invention is meant to include both active cooling by means of energy transfer as well as passive cooling, i.e. letting the temperature of the biomass slowly decrease until ambient temperature is reached. The term "cooling" or "cooled" is meant to include all possible ways of lowering the temperature of the microbial biomass. If the extraction is started before cooling of the biomass some water may be extracted together with the oil phase. The solubility of the aqueous phase into the extractant is increased when the temperature is increased. The amount of co-extracted water is very low when the temperature is decreased enough, such as to below 65° C., after the thermal pretreatment. It will not even be necessary to purify the recovered product from residual water after recovery when aiming at using the product in catalytic fuel refining.

After the thermal pretreatment the microbial biomass is subjected to extraction using a liquid hydrocarbon which is mainly water insoluble as an extractant. The biomass is contacted with the extractant preferably using mixing to enhance efficient and uniform contact. The desired lipids are extracted and separated from the microbial biomass cells. Preferably, the biomass residue is used for fodder. The extraction may be performed batchwise or continuously.

According to a preferred embodiment of the present invention, the extraction step is started immediately after the wet microbial biomass has cooled down to a temperature suitable for extraction, such as below 97° C.

In another preferred embodiment the extraction step is started before the temperature of the wet microbial biomass has reach ambient temperature, more preferably before the temperature is lowered below 40° C.

In yet another embodiment the thermal pretreatment is succeeded immediately by the extraction step in a continuous process flow.

The liquid hydrocarbon extractant is mainly water insoluble and preferably comprises low alkanes, more preferably aliphatic $C_2$-$C_8$ alkanes, most preferably propane or mixtures of low carbon number hydrocarbons, such as substantially propane. The use of propane was found especially effective and selective in combination with the thermal pretreatment.

The extraction is performed using a liquid extractant, most preferably liquid propane. This means that the pressure of the extraction vessel needs to be such that the used extractant remains in liquid form. Typically, the extraction is performed in above room temperature and e.g. if propane is used at a temperature from 60 to 95° C. the pressure needs to be at least 20 and 43 bar, respectively. Since the extraction is performed with an extractant in liquid form the temperatures and pressures cannot be such that the extractant would be in supercritical state. For example, if propane is used the temperature must be less than 97° C. in order to maintain the propane in liquid state.

The extraction is performed in a conventional manner. The yield aimed at is an efficient yield determined by the economics of the process. The ratio of used extractant such as propane to the treated cell biomass should be within reasonable limits. Preferably, this ratio, propane to cell dry weight mass, is less than 40 which sets a restriction to the total yield but lowers the consumption i.e. costs of the used propane. Optimisation of the total efficiency is within the skills of an artisan in this field applying the detailed results of the enclosed examples.

After extracting the desired lipids into the extractant this lipid containing liquid is separated from the microbial biomass and forms the product. The product containing the lipids is recovered and used further as such i.e. a mixture of extractant and lipids, or the extractant may be removed from the lipids by lowering the pressure causing the extractant to evaporate.

In one embodiment the recovered lipids in the mixture with the extractant are used as such for oil refining processes provided that said extractant is essentially propane.

In another embodiment the gasified extractant is recycled and circulated back to extraction process for reuse.

A major advantage in using the thermal pretreatment before extraction is that the extracted lipid yield is substantially increased compared to wet extraction without thermal pretreatment. The pretreatment clearly enhances the lipid transfer from microbial cells into extractant phase. In addition, providing a larger amount of extractant into contact with the microbial cell mass increases the extracted yield eliminating the effect of the possible solubility limit. These advantages are further illustrated by the examples and figures.

Moreover, the pretreatment before extraction clearly enhances the selectivity of the extracted and recovered lipids. The lipid product thus obtained contains only very low amount of metals or metal salts. Typical harmful impurities comprise Al, Cr, Cu, Fe, Ni, Pb, Zn and Mn. Preferably, the total metal content is less than 1.5 ppm, more preferably less than 1 ppm, indicating that nonpolar lipids are extracted very selectively.

The low phosphorus content in the recovered lipids, less than 10 ppm, preferably less than 5 ppm which is already suitable for catalytic fuel refining processes, more preferably less than 1 ppm, most preferably less than 0.5 ppm suggests that the amount of phospholipids co-extracted is very low. Phosphorous contents of above 15 ppm typically require subsequent further purifications steps such as degumming prior to catalytic fuel refining processes. The post treatments are facilitated by lowering the amount of phosphorous incorporated into the product.

In another aspect, the present invention provides an apparatus for carrying out the method of the invention. The apparatus for use in the above described method comprises a pressure vessel with inlet means for introduction of the wet microbial biomass and the liquid nonpolar hydrocarbon, outlet means for said hydrocarbon provided with back pressure regulation means which are connected to an extractant collection vessel for recovery of extracted lipids or a mixture of lipids with hydrocarbon.

One possible apparatus set-up is schematically depicted in FIG. 1.

The apparatus comprises a pressure vessel 1 equipped with means for agitation, such as a magnetic stirrer. The pressure vessel has regular inlet and outlet means for continuous introduction and withdrawl of wet biomass or biomass residue, respectively. In addition, the pressure vessel has inlet 2 and outlet 3 means for introduction of liquid propane and withdrawl of extractant-lipid mixture, respectively. The hydrocarbon inlet means is provided with a pressure valve 4 and the outlet means is provided with a pressure regulation means 5. Furthermore, the hydrocarbon outlet means is connected to extractant-lipid collection vessel 6 provided with further outlet means 7 for recirculation or retrival of extractant and/or extracted lipids.

The pressure vessel is suitable for withstanding temperatures of at least 300° C. and pressures of at least 150 bar. The material of the pressure vessel is corrosion resistant, preferably stainless steel. The pressure vessels are preferably treated to minimize microbial growth on the surface.

The selectivity of the method according to the present invention is believed to originate from the advantageous combination of thermal pretreatment together with the use of liquid low alkane liquid extractant, preferably liquid propane.

In yet another aspect, the present invention provides a method for recovery of lipids and low alkanes, preferably propane, or a mixture of lipids with low alkanes, preferably propane. In this system wet microbial biomass slurry, preferably comprising yeasts, filamentous fungi, moulds, algae or bacteria, is continuously introduced into a pressure vessel under continuously agitation. The temperature and the pressure of the vessel are adjusted to suitable values for the desired thermal pretreatment by regular adjusting means. After the thermal pretreatment period the temperature is decreased into the desired extraction temperature by regular adjusting means. Liquid low alkane, preferably propane, is pumped into the vessel via a tube the outlet of which extends to below the slurry surface. When the pressure of the vessel reaches the desired extraction pressure, an outlet line connected to the vessel lid is opened. Low alkane, preferably propane, is preferably continuously and countercurrently pumped through the vessel and through the aqueous microbial biomass slurry. The outlet flow from the vessel is led to a back-pressure regulator valve, which keeps the vessel pressure constant at the desired extraction pressure, and releases the flow pressure to a lower e.g. atmospheric pressure. The outlet flow from the back pressure valve is led to a extractant-lipid collection vessel wherein optionally the extracted lipids are collected while evaporated low alkane, preferably propane, is spontaneously separated from the obtained lipids and vented or recirculated. Preferably, the mixture of low alkanes, preferably propane, and lipids is used as such for fuel refining, especially catalytic refining.

In a further aspect of the present invention the recovered lipids produced by the above depicted methods are used for production of biodiesel, renewable diesel, jet fuel, gasoline or base oil components.

In a preferred embodiment the lipids recovered from the wet microbial biomass with the method according to the invention are used as feedstock for the production of biodiesel, renewable diesel, jet fuel, gasoline or base oil components and the like. By the term "biodiesel" is meant diesel which consists of fatty acid alkyl esters, and is typically produced by transesterification. In transesterification, the acylglycerols are converted to long-chain fatty acid alkyl esters, such as methyl, ethyl or propyl esters. By the term "renewable diesel" is meant fuel which is produced by hydrogen treatment of lipids, such as hydrogen deoxygenation, hydrogenation or hydroprocessing. In hydrogen treatment, acylglycerols are converted to corresponding alkanes i.e. paraffins. The paraffins can be further modified by isomerization or by other process alternatives. Renewable diesel process is optionally used to produce jet fuel and/or gasoline. In addition, cracking of lipids can be performed to produce biofuels. Furthermore, lipids are preferably used as biofuels directly without any further treatment in certain applications.

The following non-limiting examples are disclosed merely for further illustrating the present invention

EXAMPLES

Example 1

90.2 g of aqueous cell containing microbial biomass slurry, obtained from the cultivation of *Chlorella* algae, is weighed into a 200 ml pressure vessel. The cell slurry has a dry matter content of 23.8% (determined by drying at 105° C. in oven). Air is flushed out from the vessel with nitrogen gas. The vessel is then heated to 165° C. during 100 minutes and then immediately allowed to cool to approximately 60° C. (step 1).

The cell slurry is continuously agitated in the pressure vessel with a magnetic stirrer. Liquid propane is pumped into the vessel via a tube which extends to below the slurry surface. When the pressure of the vessel reaches 60 bars at 60° C., an outlet line connected to the vessel lid is opened. Propane is continuously pumped through the vessel and through the cell slurry at 4.9 g/minute (step 2). The outlet flow from the vessel is led to a back-pressure regulator valve, which keeps the vessel pressure constant at 60 bars and releases the flow pressure to atmospheric. The outlet flow from the back pressure valve is led to a bottle where the extracted lipids are collected while gasified propane is spontaneously separated from the collected lipids and vented.

The experimental set-up is schematically depicted in FIG. 1.

Figure 2:
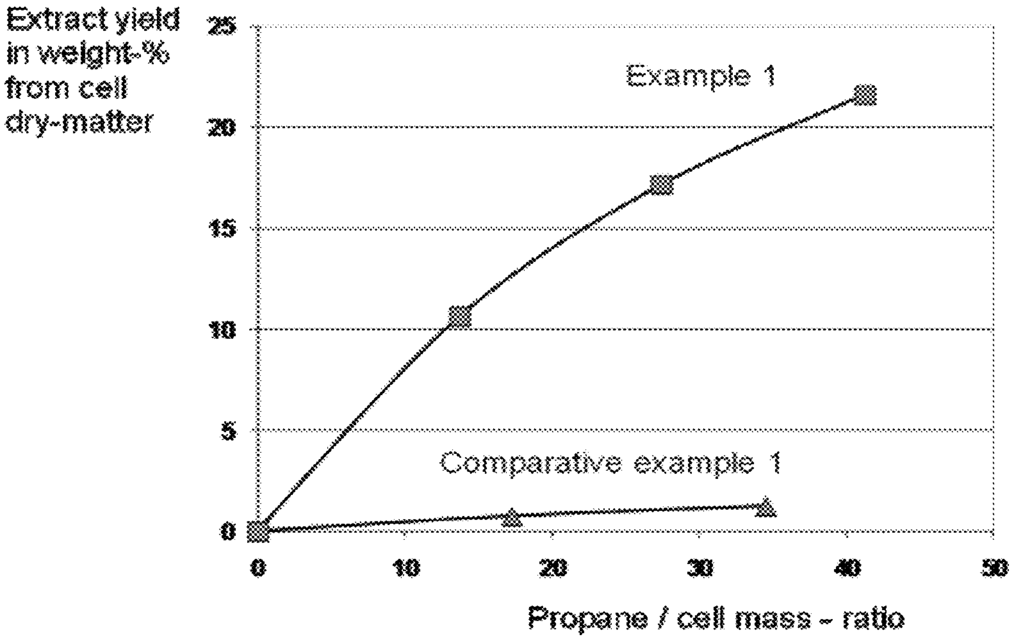
FIG. 2 shows the extract yields for *Chlorella* algae with and without the thermal pretreatment.

The extraction rate is monitored by weighing the extract collection bottle with suitable intervals. One example of an extraction curve in terms of extract yield (weight-%) calculated from the amount of recovered extracted lipids vs. dry weight of wet algae biomass as function of used propane per dry weight of wet algae biomass is shown in FIG. 2 (■).

The extract is clear with a faint orange tint. It contains 92% fatty acids in the form of triglycerides.

Example 2

The species of the microbial cells in the aqueous slurry is varied using the experimental set-up and conditions described in example 1. The species, the dry matter content of each thermally pretreated slurry and obtained extract yields are shown in table 1.

TABLE 1

| Microbial species | Microbe dry matter content % | Extract yield % of dry matter |
|---|---|---|
| *Nannochloropsis* - algae | 22.5 | 2.3 |
| *Rhodococcus* - bacteria | 58.1 | 74.0 |
| *Lipomyces* - yeast | 20.7 | 26.0 |
| *Mortierella isabellina* - filamentous fungus | 19.0 | 18.0 |

Figure 3:
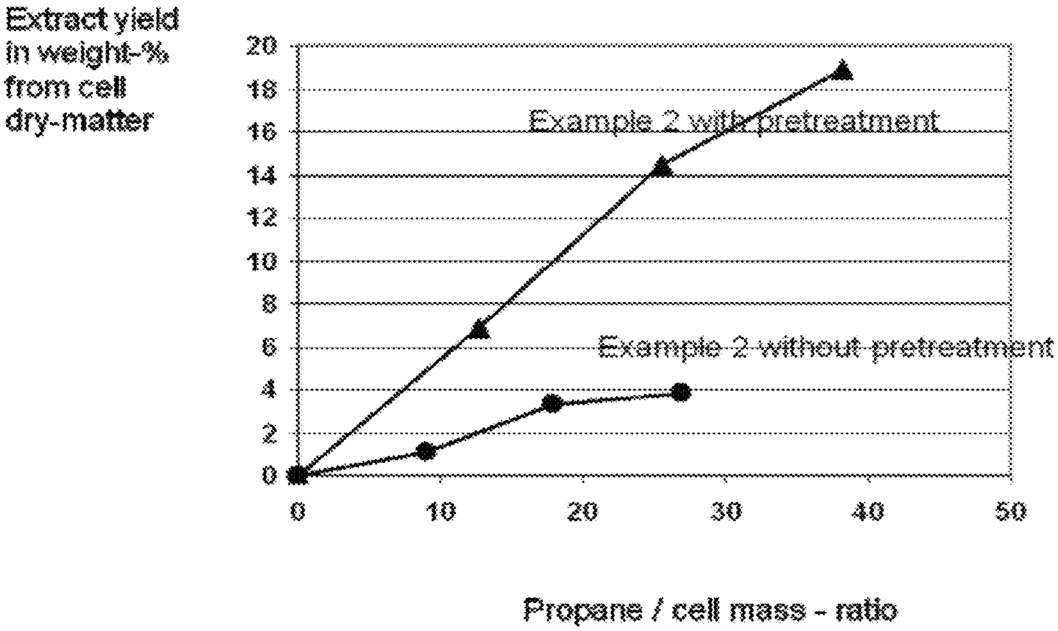
FIG. 3 shows the extract yields for *Mortierella isabellina* filamentous fungus with and without the thermal pretreatment.

The similar curve compared to that of FIG. 2 (■) now obtained from *Mortierella isabellina* filamentous fungus extracted with thermal pretreatment and a comparative extraction experiment without the thermal pretreatment are shown in FIG. 3 (▲) and (●), respectively. The overall yields from different microbial species are not comparable. Varying microbial species contain varying amounts of extractable lipids.

Example 3

The microbial biomass, thermal pretreatment temperatures and times are varied compared to values used in example 1, but the experiments are performed in the same experimental set-up of FIG. 1.

*Rhodococcus* bacteria slurry at 24.4% dry matter content is heated to 220° C. during 80 minutes time. The temperature is held at 220° C. for 40 minutes and then cooled. The obtained slurry is then extracted as described in example 1. The extract yield from the thermally pretreated *Rhodococcus* is 60% of the dry matter of the original cell slurry.

In a comparative experiment the respective *Rhodococcus* bacteria slurry is extracted without using any thermal pretreatment (see comparative example 1). The obtained extract yield in this case is only 10%.

Example 4

*Chlorella* slurry is thermally pretreated and then extracted with propane according to the experimental sep up of example 1.

The obtained oil product is analyzed according to ASTM D5185-method and the following results are obtained:

| Component | Concentration in oil mg/kg |
|---|---|
| Al | <0.1 |
| Cr | <0.1 |
| Cu | 0.3 |
| Fe | <0.1 |
| Na | <0.5 |
| Ni | <0.1 |
| Pb | <0.4 |
| Si | 21.9 |
| V | <0.1 |
| Ba | <0.1 |
| Ca | 0.2 |
| Mg | <0.1 |
| P | <0.5 |
| Zn | <0.1 |
| Mn | <0.1 |

The "<"-sign indicates that the concentration was smaller than the detection limit for that specific component.

Comparative Example 1

90.1 g of aqueous microbial biomass slurry obtained from the cultivation of *Chlorella* algae is weighed into a 200 ml pressure vessel similarly to example 1.

The slurry has a dry matter content of 22.0% (105° C., oven). The vessel is rinsed with nitrogen gas and heated to 60° C. with continuous agitation of the cell slurry with a magnetic stirrer.

Liquid propane is pumped into the vessel via a tube which extends to below the slurry surface. When the pressure of the vessel reaches 60 bars at 60° C., an outlet line connected to the vessel lid is opened. Propane is continuously pumped through the vessel and through the cell slurry at a rate of 5.7 g/minute.

The extraction rate is monitored by weighing the extract collection bottle with suitable intervals. The obtained extraction curve is shown in FIG. 2 (▲).

Comparative Example 2

Cultivated *Nannochloropsis* algae slurry is diluted with water to 10% dry matter content. The slurry is then pumped through two Microfluidizer units to disrupt the microbial cells. In the first unit the channel diameter is 200 micrometers and in the second it is 100 micrometers. The slurry is pumped through the Microfluidizer unit at 1200 bars driving pressure and the slurry is circulated through the units for 10 minutes.

Microscopy show that the *Nannochloropsis* cells are completely disrupted to micrometer-range fragments.

The disrupted cell slurry is then extracted with propane as described in comparative example 1. The obtained extract yield is only 0.53% of the dry matter of the original biomass which is much lower than the yield discussed in example 1 using the thermal pretreatment before extraction.

The result of this test proves that the enhanced yield due to thermal pretreatment is not a consequence from the disruption of the biomass cells.

The invention claimed is:

1. A method for recovery of lipids from microbial biomass, comprising:

(i) subjecting wet microbial biomass to thermal pretreatment of at least 100° C., (ii) subjecting said thermally pretreated microbial biomass to extraction using a liquid hydrocarbon as a liquid extractant, wherein the liquid extractant is the only extractact used in the extraction, and (iii) subsequently, recovering a product containing lipids, wherein said liquid extractant comprises liquid propane.

2. The method according to claim 1, wherein the dry matter content of the wet biomass is less than 70% by weight and at least 5%.

3. The method according to claim 1, wherein said wet microbial biomass is selected from the group consisting of bacteria, cyanobacteria, fungi, archaea, protists, and microscopic plants.

4. The method according to claim 1, wherein the temperature in said thermal pretreatment is at least 120° C.

5. The method according to claim 1, wherein said thermally pretreated biomass is cooled or let cool before extraction.

6. The method according to claim 5, wherein said cooling is performed at a temperature of below 97° C.

7. The method according to claim 1, wherein said recovered lipids are separated from said extractant by lowering the pressure for evaporating the extractant.

8. An oil refining process comprising utilizing recovered lipids in mixture with an extractant obtained in the method according to claim 1 as a feed of the process.

9. The process according to claim 7, wherein said extractant is circulated back to extraction step (ii).

10. A method for recovery of lipids and low alkanes or a mixture of lipids with low alkanes, from microbial biomass, the method comprising:

(i) introducing wet microbial biomass slurry continuously into a pressure vessel with continuous agitation, (ii) adjusting the pressure vessel temperature and pressure to a predetermined thermal pretreatment value for a predetermined duration, (iii) subsequently decreasing the temperature to a predetermined extraction temperature, and introducing a liquid extractant comprising liquid low alkane into said vessel via a tube an outlet of which extends to below a slurry surface, wherein the liquid extractant is the only extractact used in the extraction, and (iv) removing excess low alkane through a back pressure regulator together with extracted lipids into an extractant-lipid collection vessel wherein the pressure is decreased to achieve gaseous low alkane, and recovering lipids, or optionally a mixture of gasified low alkane and lipids therefrom, wherein the low alkane comprises propane.

11. A process for production of biodiesel, renewable diesel, jet fuel, gasoline or base oil components comprising utilizing lipids obtained in the method according to claim 1 as a feed of the process.

12. The method according to claim 1, wherein the dry matter content of the wet biomass is less than 70% by weight and at least 15%.

13. The method according to claim 1, wherein the dry matter content of the wet biomass is less than 70% by weight and at least 20%.

14. The method according to claim 1, wherein said wet microbial biomass is selected from the group consisting of algae, microalgae, plankton, planarian, bacteria, yeasts, filamentous fungi and moulds.

15. The method according to claim 1, wherein the temperature in said thermal pretreatment is from 120° C. to 300° C.

16. The method according to claim 1, wherein the temperature in said thermal pretreatment is from 150° C. to 250° C.

17. The method according to claim 1, wherein the temperature in said thermal pretreatment is from 160° C. to 220° C.

18. The method according to claim 5, wherein said cooling is performed at a temperature of below 80° C.

19. The method according to claim 6, wherein said cooling is performed at a temperature of from 40° C. to 65° C.

20. The method according to claim 10, wherein the predetermined thermal pretreatment value is 150 to 250° C., the predetermined duration is 60 to 180 minutes, and the predetermined extraction temperature is 40 to 65° C.

21. The method according to claim 1, wherein (ii) is carried out immediately after (i).

22. The method according to claim 10, wherein (iii) is carried out immediately after (ii).

* * * * *